United States Patent [19]

Cecconi

[11] Patent Number: 4,995,811
[45] Date of Patent: Feb. 26, 1991

[54] COMPONENT PART REMOVABLE PARTIAL DENTURE AND METHOD FOR DESIGNING AND MAKING SAME

[76] Inventor: Bert T. Cecconi, 3017 Charter Crest, San Antonio, Tex. 782230

[21] Appl. No.: 323,066

[22] Filed: Mar. 13, 1989

Related U.S. Application Data

[62] Division of Ser. No. 119,659, Nov. 12, 1987, abandoned.

[51] Int. Cl.$^5$ .............................................. A61C 13/26
[52] U.S. Cl. .................................... 433/190; 29/160.6; 29/527.3; 164/35; 164/76.1; 264/17; 433/167
[58] Field of Search ........................... 29/160.6, 527.3; 164/34–36, 76.1; 249/54, 62; 264/17, 18; 433/167, 171, 199.1, 200.1, 213, 190

[56] References Cited

U.S. PATENT DOCUMENTS

| | | | |
|---|---|---|---|
| 2,594,200 | 4/1952 | Muller | 433/190 |
| 2,982,024 | 5/1961 | Thompson | 433/178 |
| 3,462,837 | 8/1969 | Andrews et al. | 433/190 |

FOREIGN PATENT DOCUMENTS

4393 3/1878 Fed. Rep. of Germany ...... 433/178

OTHER PUBLICATIONS

*Ticonium 100 Premium Technique Manual*, prepared and distributed by the Ticonium Company, Division of CMP Industries, Inc., 413 No. Pearl Street, Albany, New York 12201.

Primary Examiner—P. W. Echols
Attorney, Agent, or Firm—Cox & Smith

[57] ABSTRACT

A method for designing and constructing component part removable partial dentures comprising designing the removable partial denture in tooth-supported and tissue-borne components provided with mechanical locks, waxing the design onto an investment model, casting the components, finishing the components, fitting the components onto a master cast, and locking the components together on the master cast or in the patient's mouth to form a single rigid unit using visible light cured resin around and over mechanical locks cast into the frame components.

23 Claims, 1 Drawing Sheet

COMPONENT PART REMOVABLE PARTIAL DENTURE AND METHOD FOR DESIGNING AND MAKING SAME

This application is a division of application Serial No. 119,659, filed Nov. 12, 1987 now abandoned.

BACKGROUND

This invention pertains to a method for making removable partial dentures. More particularly, the invention relates to a method for making a component part removable partial denture in which the framework is designed, waxed up, and constructed as separate parts, and the separate parts are joined together when positioned on a master cast.

Removable partial dentures and methods for casting frameworks for them have been known to dentists and technicians for many years. The conventionally used technology for constructing removable partial denture frameworks is represented by that of "Ticonium" casting, using primarily preform plastic patterns and a single sprue, as is set forth in the "Ticonium 100 Premium Technique Manual," prepared by the Ticonium Company, Division of CMP Industries, Inc., 413 N. Pearl Street, Albany, New York, 12201. The widely used "Ticonium" casting method for producing removable partial dentures suffers from the disadvantage that because of shrinkage of the metal, abberrations in the form of the casting appear during cooling. The finished product frequently fails to conform to mouth contours of the patient and may require significant adjustment. A removable partial denture cast in the conventional manner may "rock" from one side to the other, or from front to back, or may impinge upon the underlying tissue to the extent that the removable partial denture causes tissue irritation, tissue damage due to excess pressure, enamel abrasion, or increased mobility of abutment teeth.

A primary object of the present invention is to provide a component part removable partial denture which is designed as at least two independent units: a first component which is tooth-supported and a second component which is tissue-borne, for the purpose of providing optimum passive fit of the resulting framework to the supporting teeth simultaneous with optimum fit of the framework to subjacent tissue in the mouth of a patient.

Another object of the present invention is to provide component parts of a partial denture which, after they are produced, can be positioned on a master cast and locked together by mechanical locks cast into the frame components, using a high-impact visible light cured resin to form a single, rigid, functioning unit.

A further object of the present invention is to provide a method for producing a component part removable partial denture which allows for correction of casting distortions by using a visible light cured resin to lock together the components, after the components have been produced and fitted on the master cast.

Another object of the present invention is to provide a method for producing component part removable partial dentures which increases the design and construction possibilities to include designs which cannot consistently normally be produced in a single unit casting such as a removable tooth-supported bridge held in place by interproximal bracing and other framework configurations which more nearly resemble a fixed partial denture, and the use of biocompatible metal bases and major connector component parts.

Yet another object of the present invention is to produce a component part removable partial denture which, because of its precision casting and fit, can be designed to be more cosmetically acceptable to a wearer by providing fewer facial clasps.

Another object of the present invention is to provide a component part removable partial denture which can be easily removed for cleaning, and which accordingly tends to improve the oral hygiene of the patient.

A further object of the present invention is to provide a component part removable partial denture which can be constructed having a decreased amount of tissue coverage for many designs and consequently a lesser likelihood of tissue inflammation.

Another object of the present invention is to provide a component part removable partial denture which fits more precisely in a wearer's mouth, so that less movement and consequently less abrasion and tooth mobility occurs while the removable partial denture is in the patient's mouth.

Yet another object of the present invention is to provide a component part removable partial denture precisely constructed so that there is less patient awareness and greater likelihood of acceptance by patients.

A further object of the present invention is to provide a component part removable partial denture and method for constructing same wherein minor fit problems can be corrected in the patient's mouth, and it is not required to construct a new framework when such fit problems occur.

Another object of the present invention is to provide a component part removable partial denture which is more consistent in quality of fit and correctability, and less expensive to construct than the presently available fixed partial dentures, which it more closely resembles.

These and other objects, features, and advantages of the invention will become apparent to those skilled in the art in the light of the following detailed description, viewed in conjunction with the referenced drawings, of a preferred component part removable partial denture and method for constructing same according to the teachings of the present invention. The foregoing and following description of the invention is for exemplary purposes only. The true spirit and scope of the invention is set forth in the appended claims.

SUMMARY

These objects and advantages are accomplished by providing a component part removable partial denture and method for making the same comprising the steps of designing a removable partial denture in component parts on a master cast, waxing the design onto an investment cast, casting the waxed design, finishing the castings of the separate components, fitting the separate components on a master cast, and locking the components together with a high-impact visible light cured resin to form a single component part removable partial denture framework.

DETAILED DESCRIPTION OF THE DRAWINGS

Figure 1:
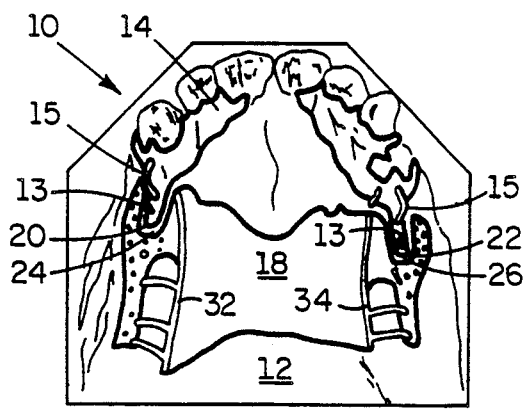
FIG. 1 is a top plan view of a component part removable partial denture design on a master cast according to the teaching of the present invention.

The method for producing a component part removable partial denture will be described in the chronological order in which the steps will take place. The first step comprises designing a component part removable partial denture, and the second step comprises making a wax pattern of the design onto an investment cast. Referring to FIG. 1, a waxed-up design for a component part removable partial denture is designated generally at reference numeral 10, received on a master cast 12 of the tooth and mouth contours of a patient (not shown). The waxed up design of FIG. 1 corresponds exactly to the castings of FIGS. 2-5 which are formed in the exact configuration of the wax during the casting process. The master cast 12 is prepared according to techniques known to those of skill in the art, and requires no special technique for the practice of the present invention. The details of design and waxing-up are selected by the dentist and technician, as will be discussed. The wax-up step is preferably done by hand, although patterns can be used where they fit into the design and are useful. Because the method of the present invention provides design possibilities and characteristics which cannot be achieved when using the conventionally available techniques for producing removable partial denture frameworks, these designs differ in some respects, such as being provided with fewer facial clasps.

In FIGS. 1-5 the invention is shown as embodied in a component part removable partial denture comprising three components. However, many variations in design and conformation are contemplated in the practice of the invention. Generally the design of a component part removable partial denture is contemplated as a tooth-supported partial which will be later joined to a separate tissue-supported partial to achieve optimum simultaneous fit of the resulting framework to both supporting teeth and subjacent tissue.

The waxed-up design disclosed in FIG. 1 is typical of designs which can be constructed according to the method of the present invention, and comprises three components: 14 and 16 which are respectively left and right tooth-supported components and tissue-borne component 18.

Figure 2:
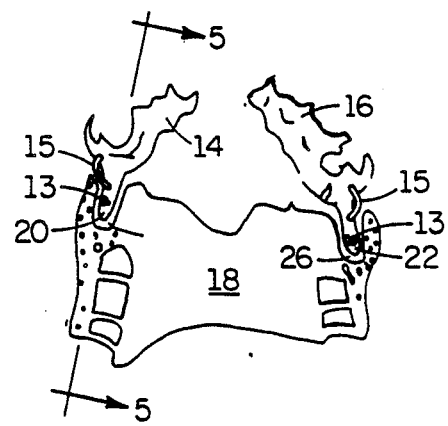
FIG. 2 is a top plan view of a casting of components of an exemplary component part removable partial denture according to the teaching of the present invention.
Figure 5:
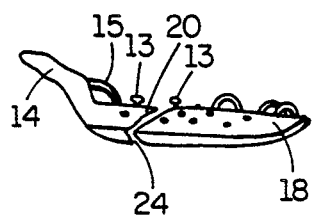
FIG. 5 is a longitudinal cross-section of an exemplary component part removable partial denture of the present invention, taken along a line 5—5 in FIG. 2.
Figure 3:
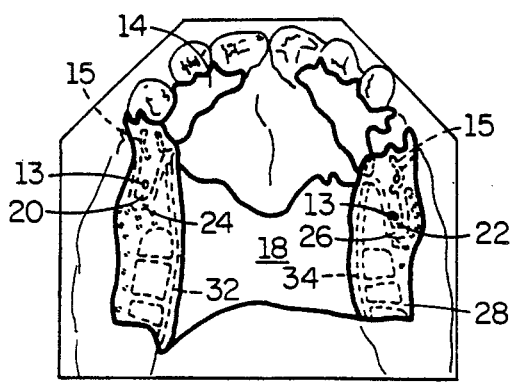
FIG. 3 is a top plan view of an exemplary component part removable partial denture constructed according to the teachings of the present invention.
Figure 4:
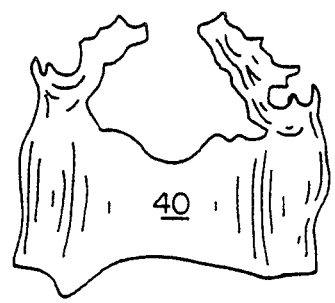
FIG. 4 is a top plan view of the component part removable partial denture of FIG. 3.

In the wax design of FIG. 1 which corresponds to the castings of FIGS. 2, 3, and 5, mechanical locks 13 and reinforcing loops 15 are provided at ends of right and left tooth-supported components 14 and 16. Extension members 20 and 22 of tooth-supported components 14 and 16, are received within slots 24 and 26 of tissue-borne component 18. Reinforcing loops 15 and discontinuous finish line 32 and 34 are provided for containment and connection of a resin base material such as high impact visible light cured resin thereto and attachment of tooth members (not shown) thereon. The waxed-up design comprises only those areas of tooth areas and subjacent tissue whereon a casting will be formed.

There is a high degree of variation in designs created for removable partial dentures. However, the method according to the teachings of the present invention permits the elimination of facial clasps in some designs, and a greater opportunity for using interproximal guide planes for bracing a tooth-supported bridge. These design possibilities increase the stability of the component part removable partial denture and also contribute to resisting lateral movement directed against abutment teeth, and providing minimum amount of movement of the component part removable partial denture during function. After the major features are waxed onto the investment cast which is an exact duplicate of the master cast 12, if it is desired to fix reinforcing rods to the wax for later attachment of tooth members, this should be done next. The present embodiment employs hand waxing to perform this task with dental casting wax although this is subject to many variations in waxing techniques well known in the art.

FIG. 2 is a top plan view of the cast component parts of the waxed design of FIG. 1. FIG. 5 discloses a saggital section taken along a line 5—5 of FIG. 2 of the components designated generally at 10. Tooth-supported components 14, and 16, and tissue borne component 18 disclosed in FIGS. 2 and 5, are separate castings. Extension members 20 and 22 are received within slots 24 and 26, but are not rigidly mounted therein during the period of time in which the components 14, 16, and 18, are being finished and fitted onto the master cast 12. The casting is customarily performed according to the "Ticonium" casting method, providing one sprue to each of the three components: right and left tooth-supported components 14 and 16 and tissue-borne component 18. In a presently preferred embodiment metal bases and major connectors are using titanium since it is the most biocompatible dental metal available and the technology to permit use of titanium in component part removable partial denture castings is also available. The decision as to where to attach the spruing leads will be affected by the general configuration of the component parts. In any event, each component will be provided with a separate spruing lead (not shown). Other casting methods known to those of skill in the art are contemplated as being within the scope of the method according to the teachings of the present invention.

The provision of spruing leads is commonly known in the art, and each separate component requires a separate spruing lead to provide molten metal to the component for casting. In the method of the present invention, each spruing lead is provided with a reservoir adjacent to the component to which the spruing lead is attached, for providing molten metal to the component as the casting of the component cools and shrinks, thus minimizing casting distortions. Use of reservoirs in spruing leads is known in the art, as the main sprue is normally provided with a reservoir.

After the next step is to finish the individual units of the component part removable partial denture. The castings of component partial denture components 14, 16, and 18 are customarily finished by cutting off the sprues, grinding, and polishing the castings using a lathe and polishing solutions as is known in the art. After the components 14, 16, and 18 are finished, they are individually fitted onto the master cast, so as to be accurately seated thereon. Finally, while in place on the master cast 12, the components are rigidly mounted together over the mechanical locks 13 and reinforcing loops 15, provided in the castings, using visible light cured resin spread over the mechanical lock areas 13, the reinforcing loops 15, and subjacent tissue areas of components 14, 16, and 18. The visible light cured resin 28 is spread within the boundaries of outside edges of the right and left tooth-supported components 14 and 16, and extending lengthwise across and around mechanical locks formed by the joinder of extension member 20 within slot 24, and extension member 22 within slot 26. The area wherein visible light cured resin 28 is received for the joining together of the component parts is bounded further by finish line 32 and finish line 34. Joinder of the components 14, 16, and 18 forms a single, rigid component part removable partial denture 40, disclosed in FIG. 4. The casting components having visible light cured resin received thereon are exposed to visible light for a total of ten to twelve minutes. This thoroughly cures the resin so that the three components 14, 16, and 18 are rigidly mounted together.

A feature of the method according to the teachings of the present invention is that it is possible to add a component to the component part removable partial denture so constructed, if a patient loses another tooth while at the same time remaining mouth and tooth contours remain unchanged.

If a problem is encountered wherein the framework of a component part removable partial denture will not seat completely on all rests, and there is a "rock" or side-to-side or front-to-back movement in the component part removable partial denture framework, the dentist can section the component part removable partial denture in the areas of mechanical locks 13, and then using visible light cured resin 28, re-seat the components and join them together again in a new, accurately fitted relationship. This adjustment can be performed in any case in which the assembled framework 40 does not fit the arch of the patient's mouth as accurately as it fit the master cast 12. The visible light cured resin 28 uniting the component parts can be cut by the dentist. The individual units can then be repositioned in the mouth and again be united with the high impact visible light cured resin. Component parts can be individually replaced if they are broken or damaged.

Generally metal is preferred over resin for tooth-supported bases, because of the surface accuracy, permanence of form, lesser weight and bulk than can be achieved using a resin-base. Further, a Titanium metal base has the property of maximum biocompatibility which is most beneficial to the subjacent tissues.

Still further, the dentist will need to spend less time adjusting the component part removable partial denture to the patient's mouth if the master cast is accurate and if the centric occlusal record is accurate as well.

Although the invention has been described in conjunction with the foregoing specific embodiment, other alternatives, variations, and modifications will be apparent to those of ordinary skill in the art. Those alternatives, variations, and modifications are intended to fall within the spirit and scope of the appended claims.

What is claimed is:

1. A method for designing and constructing a component part removable partial denture framework comprising the steps of:
   forming a model design of a partial denture in component parts on a master cast;
   making a wax pattern of said model design on an investment cast;
   forming castings on said wax pattern;
   finishing the castings in separate components;
   fitting the separate components on the master cast; and
   locking the components together to form a single component part removable partial denture framework.

2. The method of claim 1 wherein separate spruing leads are provided to each component of the design.

3. The method of claim 2 wherein each of said separate spruing leads is provided with a reservoir within said separate spruing lead adjacent said component for providing molten metal to each component during cooling thus compensating for shrinkage of the molten metal during cooling.

4. The method of claim 1 additionally comprising the step of minimizing the amount of tissue covered by the design.

5. The method of claim 1, wherein mechanical locks and reinforcing loops are provided for attachment of the components adjacent one another.

6. The method of claim 1, wherein a high impact visible light activated resin is used for said locking.

7. A method for constructing a removable partial denture metal framework comprising the following steps in the sequence set forth:
   (i) preparing a master cast of a patient's teeth and tissue;
   (ii) designing a component part removable partial denture on the master cast, said removable partial denture made of at least two components and provided with at least one mechanical lock per component;
   (iii) making a wax pattern of component part designs from said master cast onto an investment cast;
   (iv) spruing said wax pattern, providing one sprue per component part of said wax pattern;
   (v) casting the component parts;
   (vi) finishing the component parts;
   (vii) fitting the component parts on a master cast; and
   (viii) locking the component parts together.

8. The method of claim 7 wherein the components are locked together by spreading a high impact visible light cured resin around and over the mechanical locks cast into the frame component.

9. The method according to claim 7 wherein the steps thereof are repeated in sequence until a desired configuration is achieved by adding an additional component.

10. The method as recited in claim 7 wherein the casting metal is selected from the group consisting of titanium, nickel-chrome alloy, chrome-cobalt alloy, gold alloy, silver, and paladium alloys.

11. The method according to claim 7 wherein the casting metal for the tooth-supported component is selected from the group consisting of nickel-chrome alloy, chrome-cobalt alloy, gold alloy, silver, and paladium alloy, and the casting metal for the tissue-borne component is titanium.

12. A method as recited in claim 7 wherein the castings are of metal and the means for locking the components together is a visible light cured resin.

13. A method as recited in claim 7 wherein the castings are titanium and the means for locking the components together is a visible light cured resin.

14. A method for constructing a framework for a removable partial denture, comprising the steps of:
   forming a model design of the framework as separate units on a master cast, one or more said units being tooth-supported, and at least one unit being tissue-borne;

making a wax pattern of said model design of the framework on an investment cast of a patient's tooth and oral contours wherein the model comprises one or more tooth-supported components and a tissue-borne component, each component having a wax sprue lead;

casting said wax pattern into a metal framework comprising one or more tooth-supported components and a tissue-borne component, each component having a metal sprue lead;

cutting said metal sprue leads;

fitting one or more tooth-supported components on the master cast in such a manner that each component is optimally fitted and passively resting on its supporting teeth; and connecting the separate cast components together at their optimally fitted positions in relation to one another by means of a resin to form a single, rigid, passive partial denture framework.

15. The method as set forth in claim 14 wherein said framework additionally comprises a mechanical lock for securing said separate cast components to the resin.

16. A partial denture framework constructed in accordance with the method of claim 15.

17. The method as set forth in claim 14 wherein a separate component of the framework additionally comprises a reinforcing loop for securing the component to the resin, and strengthening the frame.

18. A partial denture framework constructed in accordance with the method of claim 17.

19. The method as set forth in claim 14 wherein the resin is a high-impact, visible light-cured resin.

20. The method as set forth in claim 14 wherein the resin is a visible light cured resin that bonds to the framework.

21. The method as set forth in claim 14 wherein the framework is constructed of titanium.

22. The method as set forth in claim 14 wherein the framework components are constructed of dissimilar metals.

23. A partial denture framework constructed in accordance with the method of claim 14.

* * * * *